(12) United States Patent
Müller et al.

(10) Patent No.: US 7,790,654 B1
(45) Date of Patent: Sep. 7, 2010

(54) PLANT PROTECTION AGENTS

(75) Inventors: Jacki Müller, Eferstadt (DE); Achim Zöllkau, Rheinbach (DE); Vera Pohl, Bergheim (DE); Ewa Bednarska, Bergheim (DE); Rainer Süssmann, Wolfenbüttel (DE)

(73) Assignee: Bayer CropScience Deutschland GmbH, Langenfeld (DE)

( * ) Notice: Subject to any disclaimer, the term of this patent is extended or adjusted under 35 U.S.C. 154(b) by 0 days.

(21) Appl. No.: 09/403,192

(22) PCT Filed: Mar. 31, 1998

(86) PCT No.: PCT/EP98/01870
§ 371 (c)(1),
(2), (4) Date: Jan. 31, 2000

(87) PCT Pub. No.: WO98/46075
PCT Pub. Date: Oct. 22, 1998

(51) Int. Cl.
*A01N 47/10* (2006.01)
(52) U.S. Cl. .................................................. 504/157
(58) Field of Classification Search ................. 504/118, 504/157
See application file for complete search history.

(56) References Cited

U.S. PATENT DOCUMENTS

| | | | | |
|---|---|---|---|---|
| 4,185,992 | A * | 1/1980 | Gilmour | 504/279 |
| 5,658,851 | A * | 8/1997 | Murphy et al. | 504/362 |
| 6,436,439 | B1 | 8/2002 | Landham et al. | |
| 6,656,883 | B1 | 12/2003 | Vogt et al. | |

FOREIGN PATENT DOCUMENTS

| | | | |
|---|---|---|---|
| DE | 42 948 | | 8/1937 |
| DE | 40 29 304 A1 | | 3/1992 |
| DE | 43 29 974 A1 | | 3/1995 |
| EP | 0465899 B1 | | 8/1995 |
| GB | 2245494 | * | 1/1992 |
| JP | 63023804 | * | 2/1988 |
| WO | 9518531 | * | 7/1995 |
| WO | WO 95/18531 | | 7/1995 |
| WO | WO 96/03871 | | 2/1996 |

OTHER PUBLICATIONS

Tadros, Tharwat F., "Surfactants in Agrochemicals", *Marcel Dekker, Inc.*, p. 155.
Foy. Chester L., "Pesticide Formulation and Adjuvant Technology", *CRC Press*, p. 85.
Flabe, Dr., Jürgen, "Römpp Chemie Lexikon", *Georg Thieme Verlag Stuttgart*, pp. 2233-2234.
Büchel, K.H., "Pfianzenschutz and Schädlingsbekämpfung", *Georg Thieme Verlag Stuttgart*, p. 198 (1977).

* cited by examiner

*Primary Examiner*—Alton N Pryor
(74) *Attorney, Agent, or Firm*—Victor N. King; Speckman Law Group PLLC

(57) ABSTRACT

Crop protection compositions, formulated as powder, granules or water-based, of active compounds having foliar or systemic action are characterized in that they comprise, in the case of herbicide preparations, at least one herbicide from the groups of the urea derivatives or sulphonylureas, the carbamates, biscarbamates, diphenyl ethers, pyridolylacetic acid derivatives, pyridazines, triazines, triazinones, uracils, benzofuran derivatives, glyphosate or glufosinate, in the case of fungicide preparations, at least one fungicide from the group of the morpholines, azoles, phthalimides or piperidines, in the case of insecticide preparations, at least one insecticide from the group of the pyrethroids, carbamates or organophosphates, or possible salts or esters of the abovementioned groups of active compounds, at least one inorganic adsorbent and at least one surfactant, preferably from the group of the ethoxylated $C_6$-to $C_{20}$-alcohols, preferably $C_8$- to $C_{16}$-alcohols, the ethoxylated castor oils or the alkyl ether sulphates.

21 Claims, 2 Drawing Sheets

PLANT PROTECTION AGENTS

TECHNICAL FIELD OF THE INVENTION

The present invention provides crop protection compositions comprising active compounds having foliar or systemic action which make it possible to widen the activity spectrum and the activity by employing a surfactant/silica gel mixture.

In the terminology of the present application, crop protection compositions are ready-to-use preparations of active compounds which are directed in particular against animal, microbial or plant pathogens of useful or crop plants.

BACKGROUND OF THE INVENTION

It is very common and has been known for a long time to add colloidal silicic acids in the field of the formulations of crop protection agents. The use is described sufficiently in the corresponding literature.

The use known from the prior art is limited to the use of the silica gels as so-called "inert" cocomponents in crop protection preparations. Thus, for example, the use of silica gels as auxiliaries for preparing dispersible suspensions is described in Bühel "Pflanzenschutz und Schädlingsbekämpfungsmittel", 1977, page 198. In "Surfactants in Agrochemicals" 1995, page 155, Tadros describes the use of silica gels as additives for suspension concentrates to prevent sedimentation and caking. The use of silica gel as filler is described in Foy and Pritchard in "Pesticide Formulation and Adjuvant Technology", 1996, page 85.

In Römpp, "Chemie Lexikon", 1995, page 2233, under the entry "Kieselgele", likewise only the properties and uses which are already known, inter alia as thixotropic agent, are described.

An increase in activity or a widening of the activity spectrum of, for example, herbicides having foliar action on weeds outside the known area of use on addition of silica gels has not been described and was also not to be expected.

To improve the activity of known crop protection agents, the prior art proposes specific additives or specific cocomponents developed for this purpose. In general, mineral oils and vegetable oils and their derivatives, and also specific surfactants, for example polysaccharides, ethoxylated triglycerides, ethylene oxide or propylene oxide copolymer adducts with ethylenediamine as central starter unit, polyethoxylated fatty acids and amides thereof and also ethoxylated alkylaryl alcohols having typically 6-10 oxyethylene units are employed here.

The amount of such additives or bioactivators that is required varies between 100 g/l of ready-to-use preparation to from 2 to 3 l per ha, for example in the case of the mineral and vegetable oils as tank mix partners of the herbicides having foliar action.

It was not possible with any of these products to extend the activity spectrum of, for example, active compounds employed as herbicides to other weeds and to improve the activity at the same time.

Recent studies have shown that the use of aqueous suspension concentrates generally offers advantages compared to emulsions. Thus, the use of solvents which are toxicologically and ecotoxicologically objectionable, such as, for example, isophorone, cyclohexanone, xylenes and acetophenone, can be dispensed with.

Moreover, the concentration of the active compounds can be considerably increased (cf. DE 43 29 974). These advantages reduce, for example, packaging, transport and also storage costs considerably.

SUMMARY OF THE INVENTION

It was the object of the present invention to improve the activity spectrum and the activity of known active crop protection agents and to provide novel, more effective crop protection compositions.

This object was surprisingly achieved by the features of the main claim. Preferred embodiments are characterized in the subclaims.

In addition to the expected effects when rendering suspensions thixotropic and on use as a filler in powders and granules, the simultaneous use of the inorganic adsorbents selected according to the invention, preferably the use of silicic acid, alumosilicates and/or aluminium oxides in combination with specific surfactants in powders, granules and aqueous suspension concentrates of active compounds having foliar or systemic action resulted in an unexpected increase in the activity potential and in a widening of, in particular, the weed application spectrum, compared with conventionally formulated emulsion preparations and suspension concentrates.

DETAILED DESCRIPTION OF THE INVENTION

Figure 1:
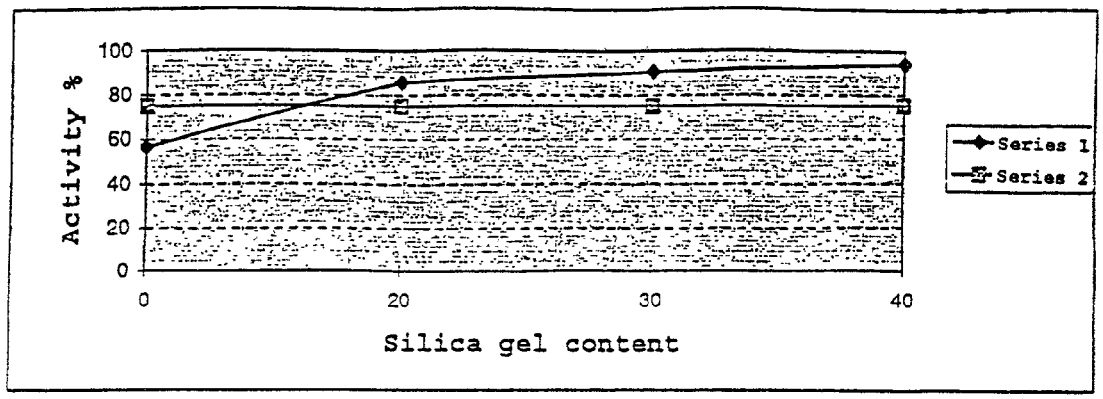
FIG. 1 shows the correlation of activity (%) and silica gel content (g/l) for a phenmedipham/desmedipham (PMP/DMP) suspension concentrate mixture.

The silicic acid used can be colloidal silicic acid, generally referred to as silica gel, but also the so-called pyrogenic silicic acid, generally referred to as Aerosil. Aluminium oxide in all its modifications and hydrated forms and alumosilicates, in particular the specific surfactants selected according to the invention likewise exhibited a surprising activity-increasing effect and resulted in a widening of the application spectrum. Preference is given to using silica gel. The inorganic adsorbents selected according to the invention can be added in proportions of from 0.5 to 25.0% by weight, preferably in proportions of from 2.0 to 15.0% by weight, to the novel crop protection compositions according to the invention.

The surfactants to be employed according to the invention are selected from the group of ethoxylated $C_6$ to $C_{20}$ alcohols, preferably $C_6$-$C_{16}$, of the ethylene/propylene oxide block copolymers, if appropriate comprising ethylene diamine as starter unit, and of the alkyl ether sulphates and their combinations. It is also possible to employ ethoxylated castor oil. Preference is given to using ethoxylated tridecanols having from 5 to 13 ethylene oxide units, sodium, potassium or ammonium alkyl ether sulphates, in particular sodium, potassium or ammonium fatty alcohol diglycol ether sulphates or mixtures of these surfactants. Particular preference is given to using the surfactants Volpo T/785, Volpo T/10, Genapol LRO, Emulsogen, Pluronic types or mixtures of these surfactants, which are known per se. The proportion of surfactant in the crop protection compositions according to the invention is from 5.0 to 40.0% by weight, preferably between 10.0 and 25% by weight.

The sum of the proportions of adsorbents selected according to the invention and surfactants selected according to the invention is from 5.5 to 45.0% by weight, preferably from 15.0 to 25.0% by weight.

As herbicidally active compounds, the novel crop protection compositions according to the invention comprise herbicides which have both foliar action and soil and foliar action from the groups of the urea derivatives, the carbamates, biscarbamates, diphenyl ethers, pyridolylacetic acid derivatives, pyridazines, triazines, triazinones, uracils, sulphonylureas, benzofuran derivatives and also glufosinate and glyphosate, and their salts or esters, and also mixtures of some selected active compounds. Preference is given to using phenmedipham (PMP), desmedipham (DMP), metamitron and/or ethofumesate. Suitable fungicidally active compounds are morpholines, azols, phthalimides or piperidines, suitable insecticides are pyrethroids, carbamates or organophosphates, and the possible salts or esters and also mixtures of selected abovementioned active compounds. The proportion of active compound in the crop protection compositions according to the invention is from 5.0 to 75.0% by weight, preferably from 15.0 to 55.0% by weight.

In addition to these components, the crop protection composition according to the invention may comprise auxiliaries and/or carriers known per se which are customarily used for suspension concentrates. Antifreeze agents, stabilizers, antifoams, wetting agents and dispersants and also, if appropriate, other fillers may be mentioned by way of example. Reference may also be made here to DE 43 29 974. The wetting agent and dispersant can be selected, for example, from the groups of the phosphated di- or tristyrenephenol ethoxylates in the phosphate form and/or of the lignin sulphonates. Preference is given to using ethoxylated tristyrenephenol phosphates, sodium, potassium, calcium, magnesium, zinc or ammonium lignin sulphonates, in particular mixed calcium/magnesium/zinc lignin sulphonate salts, or mixtures of these agents. Particular preference is given to Tensiofix LX Special, Soprophor FL, Soprophor FL 60 or mixtures of these agents.

The crop protection compositions according to the invention are prepared by processes known per se, for example the wet milling principle. To this end, the individual components (active compounds and auxiliaries) are finely ground with an appropriate amount of water in a suitable apparatus, for example a bead mill.

The components are preferably adjusted to a degree of fineness of from 0.5 to 20 μm, in particular to a degree of fineness of <10 μm. In the case of solid preparations (granules or powders), use is likewise made of methods corresponding to the prior art.

In the formulation form/appearance of a suspension concentrate, the crop protection compositions according to the invention exhibit, in addition to the known toxicological and ecotoxicological advantages, surprisingly an additionally increased biological potential in the control of weeds which as yet has not been able to be controlled using equivalent application rates of known preparations.

Thus, compositions prepared using the adsorbent/surfactant combination according to the invention make it possible for the first time to employ crop protection agents from the group of the carbamates and biscarbamates for controlling camomile species, for example *Matricaria chamomilla* (MATCH) and *Matricaria inodora* (MATIN). Hitherto, it has not been possible to control camomile species satisfactorily, either using the active compound desmedipham, or using the active compound phenmedipham, or using a 1:1 mixture or a combination of the abovementioned active compounds with ethofumesate (cf. the examples below). Satisfactory control has hitherto only been possible by using further herbicides (for example metamitron).

Furthermore, it was possible to reduce the amount of composition applied by from 10 to 20% at the same activity, for example, by employing the crop protection compositions according to the invention from the field of the triazinones, for example in the cultivation of sugar beet, as shown by the example below.

The table shows the scores obtained in a herbicide trial in sugar beet. A conventional metamitron SC was compared, at an equivalent application rate in l/ha, but with reduced amounts of active compound per ha, with a metamitron SC according to the invention. (6.5 l/ha×700 g/l=4550 g/ha compared with 6.5 l/ha×550 g/l=3575 g/ha corresponding to −21.4%)

TABLE 1

| Preparation | l/ha | CHEAL | VIOAR | POLSS | MATCH | GALAP | MEAN |
|---|---|---|---|---|---|---|---|
| metamitron 700 g/l SC | 6.5 | 98 | 92 | 90 | 100 | 73 | 91 |
| metamitron SC according to the invention, 550 g/l | 6.5 | 100 | 88 | 96 | 100 | 80 | 93 |

The combination of two active compounds having foliar action, i.e. phenmedipham and desmedipham, whose known activity spectra are limited to broad-leaved weeds, with insufficient activity against camomile, showed, at an identical application rate of active compound per ha, a considerably improved activity compared to an emulsion The following examples and recipes are intended to illustrate the invention, without limiting it.

| Suspension concentrate A: | |
|---|---|
| | g/l |
| desmedipham | 160 |
| phenmedipham | 160 |
| Soprophor FL 60 | 25 |
| Volpo T/7 85 | 100 |
| Genapol LRO | 30 |
| Tensiofix LX Spezial | 5 |
| silica gel SM 614 | 40 |
| antifreeze agent | 40 |
| stabilizer | 1 |
| antifoam | 5 |
| water | ad 1 l |

| Suspension concentrate B | |
|---|---|
| | g/l |
| desmedipham | 35 |
| phenmedipham | 100 |
| ethofumesate | 200 |
| Pluronic | 55 |
| Genapol LRO | 150 |
| silica gel SM 614 | 35 |
| antifreeze agent | 60 |
| stabilizer | 0.5 |
| antifoam | 5 |
| water | ad 1 l |

| Suspension concentrate C: | |
|---|---|
| | g/l |
| desmedipham | 320 |
| Soprophor FL | 30 |
| Volpo T/7 85 | 135 |
| Genapol LRO paste | 15 |
| Tensiofix LX Spezial | 3 |
| silica gel SM 514 | 37 |
| antifreeze agent | 45 |
| stabilizer | 0.5 |
| antifoam | 5 |
| water | ad 1 l |
| antifreeze agent | 45 |
| stabilizer | 0.5 |
| antifoam | 5 |
| water | ad 1 l |

| Suspension concentrate D: | |
|---|---|
| | g/l |
| phenmedipham | 320 |
| Soprophor FL 60 | 45 |
| Volpo T/10 | 120 |
| Genapol LRO | 45 |
| Tensiofix LX Spezial | 5 |
| silica gel SM 614 | 45 |
| antifreeze agent | 40 |
| stabilizer | 1.0 |
| antifoam | 7 |
| water | ad 1 l |
| antifreeze agent | 40 |
| stabilizer | 1.0 |
| antifoam | 7 |
| water | ad 1 l |

| Suspension concentrate E: | |
|---|---|
| | g/l |
| metamitron | 550 |
| Hoechst LFS | 35 |
| Genapol LRO | 40 |
| Volpo T/10 | 120 |
| silica gel Tixosil 38A | 37 |
| antifreeze agent | 35 |
| antifoam | 5 |
| stabilizers | 1 |
| water | ad 1 l. |

EXAMPLE 1

Correlation of activity (%) and silica gel content (g/l) for a PMP/DMP mixture:

The effect of the addition of silica gel on the activity potential of a crop protection composition becomes evident when comparing a basic recipe without and with varying silica gel content. A phenmedipham/desmedipham suspension concentrate (PMP/DMP) having varying silica gel content was compared with a phenmedipham/desmedipham emulsion concentrate Betanal® AM 11 EC from Hoechst Schering AgrEvoGmbH (Betanal AM 11 comprises PMP/DMP in a ratio of 1:1) without silica gel. The results are shown in Table 2 and FIG. 1.

TABLE 2

Correlation of activity (%) and silica gel content (g/l) for a PMP/DMP mixture at the same application rate of active compounds/ha

| | | | | |
|---|---|---|---|---|
| Silica gel content in a suspension according to the invention (series 1) | 0 | 20 | 30 | 40 |
| Activity % | 56.6 | 85.8 | 90.8 | 94.2 |
| *Betanal AM 11 EC without silica gel (series 2) | 0 | 0 | 0 | 0 |
| Activity % | 75 | 75 | 75 | 75 |

EXAMPLE 2

Comparison of the activity of two crop protection compositions

Figure 2:
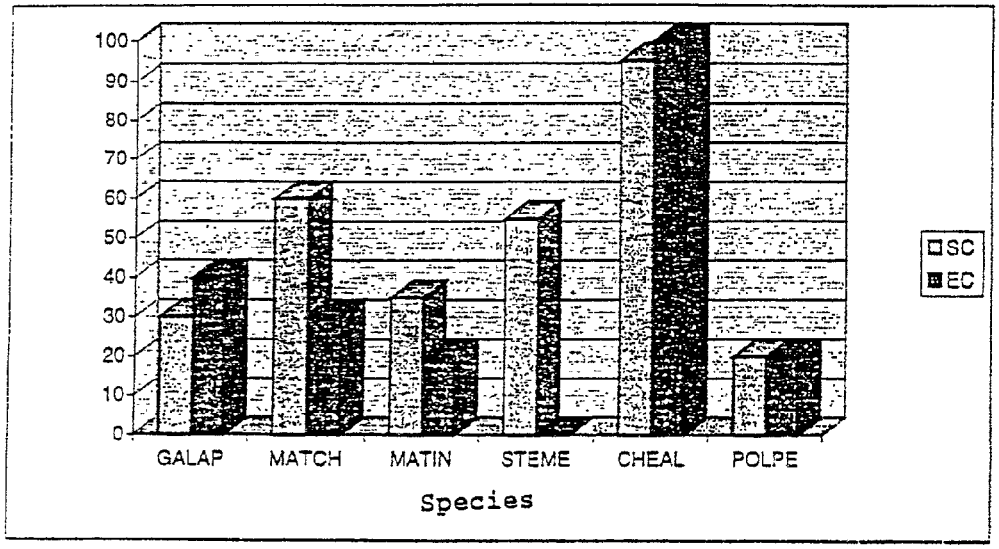
FIG. 2 illustrates a comparison of activity of two crop protection compositions in various plant species.

A crop protection composition according to the invention (suspension concentrate C; SC C) which comprised 320 g/l of desmedipham was compared with a crop protection composition known from the prior art (Betanal® AM from Hoechst Schering AgrEvo GmbH; Betanal AM comprises only desmedipham; EC), which comprised 160 g of desmedipham/l. 0.75 ml of the suspension concentrate according to the invention (SC C)/ha and 1.5 l of Betanal AM (EC)/ha were applied (this corresponds to equivalent amounts/ha). The results are shown in Tab. 3 and FIG. 2.

TABLE 3

Comparison of the activity of a suspension according to the invention with *Betanal AM

| | Activity [%]/species | | | | | | |
|---|---|---|---|---|---|---|---|
| Type | GALAP | MATCH | MATIN | STEME | CHEAL | POLPE | Mean |
| SC C | 30 | 60 | 35 | 55 | 95 | 20 | 49.2 |
| EC | 40 | 30 | 20 | 0 | 100 | 20 | 35 |

GALAP: *Galium aparine*
MATCH: *Matricaria chamomilla*
MATIN: *Matricaria inodora*
STEME: *Stellaria media*
CHEAL: *Chenopodium album*
POLPE: *Polygorium persicara*

EXAMPLE 3

Figure 3:
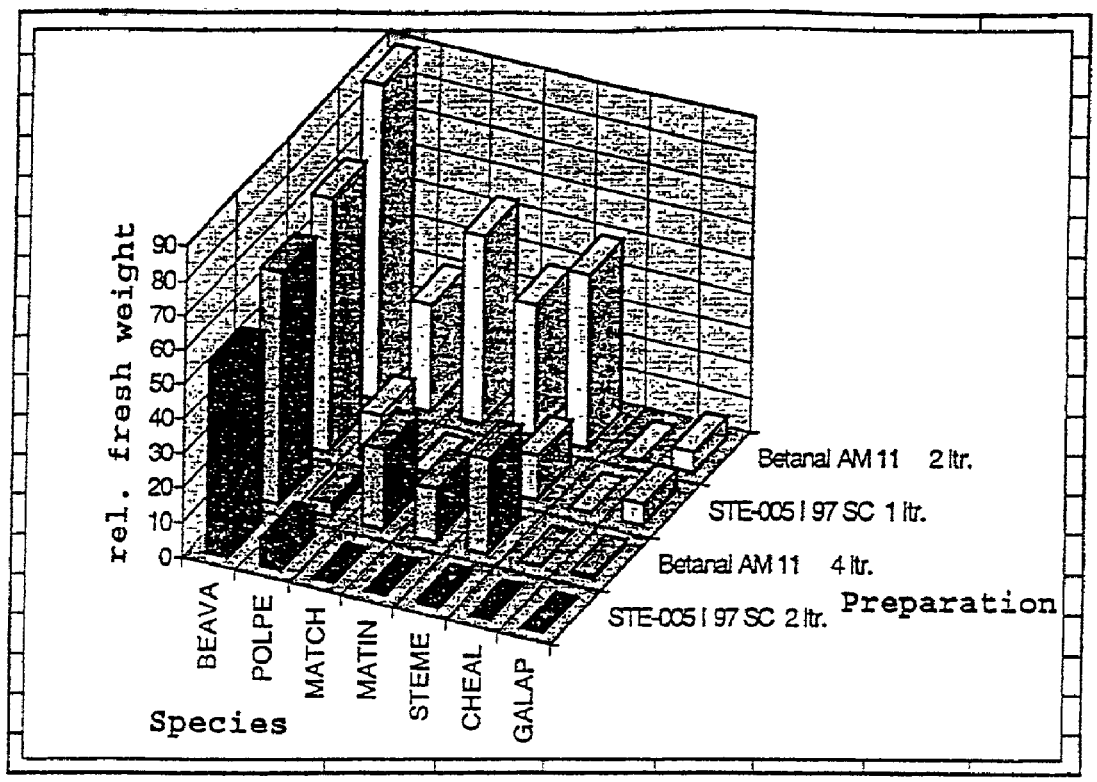
FIG. 3 shows a comparison of activity of the crop protection compositions at different application rates.

Comparison of the activity at different application rates:

The substantially improved activity of the crop protection compositions according to the invention becomes evident when the relative fresh weights of the weeds are compared. The suspension A according to the invention (SC A) was compared with Betanal® AM 11 from AgrEvo which comprised DMP and PMP in a ratio of 1:1. Fresh weight is defined as the mass of the above-ground parts of the plants. Relative fresh weight is defined as the mass of the above-ground parts of the plants of a treated sample in comparison with the mass of an untreated control sample (=100%). The results are shown in Table 4 and FIG. 3.

TABLE 4

Comparison of the relative fresh weights at two different application rates

| Product | Application rate [l/ha] | BEAVA | POLPE | MATCH | MATIN | STEME | CHEAL | GALAP |
|---|---|---|---|---|---|---|---|---|
| Betanal AM 11 | 4 | 67 | 4 | 23 | 15 | 27 | 0 | 1 |
| SC A | 2 | 55 | 8 | 0 | 0 | 1 | 0 | 0 |
| Betanal AM 11 | 2 | 90 | 31 | 54 | 38 | 50 | 0 | 6 |
| SC A | 1 | 73 | 14 | 1 | 2 | 13 | 0 | 6 |

GALAP: *Galium aparine*
MATCH: *Matricaria chamomilla*
MATIN: *Matricaria inodora*
STEME: *Stellaria media*
CHEAL: *Chenopodium album*
POLPE: *Polygorium persicara*
BEAVA: *Beta vulgaris*

EXAMPLE 4

Example 4 shows a comparison of the activity of approved emulsion concentrates (Betanal AM and Betanal AM 11) with suspension concentrate according to the invention having a proportion of silica gel of 40 g/l or 20 g/l at different application rates. Both the integral (6 species) and the species-specific activity is substantially increased when the composition according to the invention is employed.

TABLE 5

| Variant | Active compounds (g/l) | Application rate (l/ha) | Activity % ⌀* 6 species | Activity % Matin** | Activity % Match*** |
|---|---|---|---|---|---|
| Standard EC Betanal® AM11 | 80 + 80 DMP + PMP | 1 | 22.6 | 0 | 0 |
| | | 2 | 46.5 | 45 | 10 |
| | | 4 | 75 | 75 | 50 |
| Suspension according to the invention SC A (Code No. 8102-005I97 comprising 40 g of silica gel/l) | 160 + 160 DMP + PMP | 0.5 | 46.6 | 65 | 55 |
| | | 1 | 82.3 | 97 | 97 |
| | | 2 | 94.2 | 100 | 100 |
| Standard EC | 160 | 1 | 20 | 0 | 30 |
| Betanal® AM | DMP | 1.5 | 35 | 20 | 30 |
| | | 2 | 46.7 | 20 | 40 |
| Suspension according to the invention | 320 DMP | 0.5 | 35.8 | 20 | 60 |
| | | 0.75 | 49 | 35 | 60 |
| SC C (Code No. 8101-006197 comprising 20 g of silica gel/l) | | 1 | 62 | 75 | 70 |

*Galium aparine, matricaria chamomilla, matricaria inodore, stellaria media, Chenopodium album and polygonum persicara
**Matricaria inodora
***Matricaria chamomilla
Betanal® registered trademark of Hoechst Schering AgrEvo GmbH

EXAMPLE 5

Comparison of approved emulsion concentrates with suspension concentrates according to the invention comprising the active compounds ethofumesate, phenmedipham and desmedipham with a proportion of silica gel of 40 g/l.

TABLE 6

|  | l/ha | GALAP | MATCH | MATIN | STEME | CHEAL | POLPE |
|---|---|---|---|---|---|---|---|
| Betanal Progress comprising PMP 75; DMP 25; Etho 150 g/l | 1 | 75 | 90 | 99 | 75 | 99 | 80 |
| SC according to the invention comprising PMP 100; DMP 33; Etho 200 g/l | 0.75 | 75 | 95 | 100 | 88 | 100 | 90 |

Table 7 below states the type and group association of the cocomponents used.

TABLE 7

| Cocomponent | Type | Chem. group |
|---|---|---|
| Volpo T 7 85 and T 10 | Wetting agent | Polyethoxylated alcohols |
| Genapol LRO | Wetting agent | Fatty alcohol diglycol ether sulphate Na salt |
| Tensiofix LX Special | Dispersant | Lignin sulphonate |
| Soprophor Fl and Fl 60 | Dispersant | Ethoxylated tristyrene-phenol phosphate |
| Emulsogen | Wetting agent | Ethoxylated castor oil |
| Pluronic | Dispersant | Ethylene oxide/propylene oxide block polymer |
| Hoechst LFS | Dispersant | Poly(arylalkyl)phenol polyethylene glycol phosphoric ester, triethanolammonium salt |

What is claimed is:

1. A crop protection composition of active compounds having foliar or systemic action, comprising:
   (a) at least one active compound selected from biscarbamate herbicides;
   (b) at least one inorganic adsorbent comprising a silicic acid;
   (c) at least one surfactant selected from an ethoxylated tridecanol having 5 to 13 ethoxy units; and
   (d) at least one additional active compound selected from the group consisting of: metamitron and ethofumesate,
wherein said composition is formulated as an aqueous suspension concentrate.

2. The crop protection composition according to claim 1 wherein said silicic acid is selected from the group consisting of: colloidal silicic acid, which is silica gel, and pyrogenic silicic acid (Aerosil™).

3. The crop protection composition according to claim 2 wherein said silica gel has an $SiO_2$ content of at least 95% and a specific surface area of from 100 to 700 $m^2/g$.

4. The crop protection composition according to claim 2 wherein said silica gel has a specific surface area of from 130 to 250 $m^2/g$.

5. The crop protection composition according to claim 1 wherein the proportion of said at least one surfactant is in the range of 5 to 40% by weight.

6. The crop protection composition according to claim 1, wherein the biscarbamate is selected from the group consisting of: phenmedipham, desmedipham, and a mixture of phenmedipham and desmedipham.

7. The crop protection composition according to claim 1, further comprising auxiliaries selected from the group consisting of: antifreeze agents, stabilizers, antifoams, wetting agents, and dispersants.

8. The crop protection composition according to claim 1 wherein proportion of said at least one inorganic adsorbent is within the range of 0.5 to 25% by weight.

9. The crop protection composition according to claim 1 wherein proportion of said at least one inorganic adsorbent is within the range of 2.0 to 15.0% by weight, proportion of said surfactant is within the range between 10 to 35% by weight, and proportion of said herbicide is within the range of 5.0 to 75.0% by weight.

10. The crop protection composition according to claim 7 wherein the active compounds and the auxiliaries are finely ground and adjusted to a degree of fineness from 0.5 to 20 μm.

11. The crop protection composition according to claim 10 wherein said active compounds and the auxiliaries are adjusted to a degree of fineness of <10 μm.

12. A process for preparing a crop protection composition according to claim 7 wherein the active compounds and the auxiliaries are finely ground and adjusted to a degree of fineness in the range of 0.5 to 20 μm.

13. The process according to claim 12 wherein said active compounds and the auxiliaries are finely ground and adjusted to a degree of fineness of <10 μm.

14. The water-based crop protection composition according to claim 1, wherein the sum of proportions of said at least one inorganic adsorbent and of said at least one surfactant is 5.5 to 45.0% by weight.

15. The water-based crop protection composition according to claim 1, wherein the sum of proportions of said at least one inorganic adsorbent and of said at least one surfactant is 15.0 to 25.0% by weight.

16. A water-based crop protection composition of active compounds having foliar or systemic action, comprising:
   (a) at least one active compound selected from biscarbamate herbicides;
   (b) at least one inorganic adsorbent comprising a silicic acid;
   (c) at least one surfactant comprising an ethoxylated tridecanol having 5 to 13 ethoxy units;
   (d) at least one additional active compound selected from the group consisting of: metamitron and ethofumesate; and
   (e) water,
wherein total proportion of active compounds in the crop protection composition is from 5.0 to 75.0% by weight, and wherein said composition is formulated as an aqueous suspension concentrate.

17. The water-based crop protection composition according to claim 16, further comprising auxiliaries selected from the group consisting of: antifreeze agents, stabilizers, antifoams, wetting agents, and dispersants.

18. A water-based crop protection composition consisting of:

(a) at least one active compound selected from biscarbamate herbicides;
(b) at least one inorganic adsorbent comprising a silicic acid;
(c) at least one surfactant comprising an ethoxylated tridecanol having 5 to 13 ethoxy units;
(d) at least one additional active compound selected from the group consisting of: metamitron and ethofumesate;
(e) auxiliaries selected from the group consisting of: antifreeze agents, stabilizers, antifoams, wetting agents, and dispersants; and
(f) water, wherein said composition is formulated as an aqueous suspension concentrate.

19. The water-based crop protection composition according to claim 18, wherein proportion of said at least one inorganic adsorbent is from 0.5 to 25.0% by weight, proportion of said at least one surfactant is from 5.0 to 40.0% by weight, and proportion of said active compounds is from 5.0 to 75.0% by weight.

20. The water-based crop protection composition according to claim 18, wherein proportion of said at least one inorganic adsorbent is from 2.0 to 15.0% by weight, proportion of said at least one surfactant is from 5.0 to 40.0% by weight, and proportion of said active compounds is from 15.0 to 55.0% by weight.

21. The water-based crop protection composition according to claim 18, wherein the sum of proportions of said at least one inorganic adsorbent and of said at least one surfactant is 5.5 to 45.0% by weight.

* * * * *